United States Patent [19]

Serpa

[11] Plant 5,183

[45] Jan. 24, 1984

[54] LIQUIDAMBAR TREE, FREMONT

[76] Inventor: Frank J. Serpa, 715 Seville Pl., Fremont, Calif. 94539

[21] Appl. No.: 394,397

[22] Filed: Jul. 1, 1982

[51] Int. Cl.[3] ..... A01H 5/12

[52] U.S. Cl. ..... Plt./51

[58] Field of Search ..... Plt./51

*Primary Examiner*—Robert E. Bagwill

*Attorney, Agent, or Firm*—Townsend and Townsend

EXEMPLARY CLAIM

A new and distinct variety of liquidambar tree characterized by being truly evergreen. The leaves fall during their second year after the new year's leafy growth has emerged.

5 Drawing Figures

1

This invention relates to a new and distinct variety of liquidambar tree. The proposed variety name is "Fremont." The new variety is the result of a selection from a seedling block noticed and carefully observed since its germination in 1966, substantially as herein described.

The new variety of liquidambar tree was first observed in a seedling block where four different Liquidambar trees of three differing species, *Liquidambar styraciflua, Liquidambar orientalis,* and *Liquidambar formosana,* had been planted. The trees were purposely hybridized, the seed was permitted to drop, and the dropped seeds eventually germinated. Upon careful observation of these seedlings I noticed seven of them which appeared to be evergreen; that is, they retained their leaves throughout the year. All of the seven have been disposed of except for the new variety described below and for which a patent is being sought. The exact parentage of and species of the new variety are unknown. The new variety has been asexually reproduced at my direction at a nursery in Fremont, Calif. from cuttings from the mother tree.

The main distinguishing feature of the new variety is that it is evergreen. The leaves of the new variety drop when they are fully mature, during the course of the following year, rather than the fall of the first year as do all other liquidambars. The leaves drop throughout the year, having disappeared under a canopy of fresh new growth from the current year, thus giving the new variety its special evergreen characteristic. In 35 years of careful observation of liquidambars, this is the only truly evergreen liquidambar tree which I have ever noticed.

The following description of this new liquidambar cultivar is in accordance with the Exotica Horticultural

2

Color Guide published by Roehrs Company of Rutherford, N.J., 7th Edition 1974.

Figure 1:
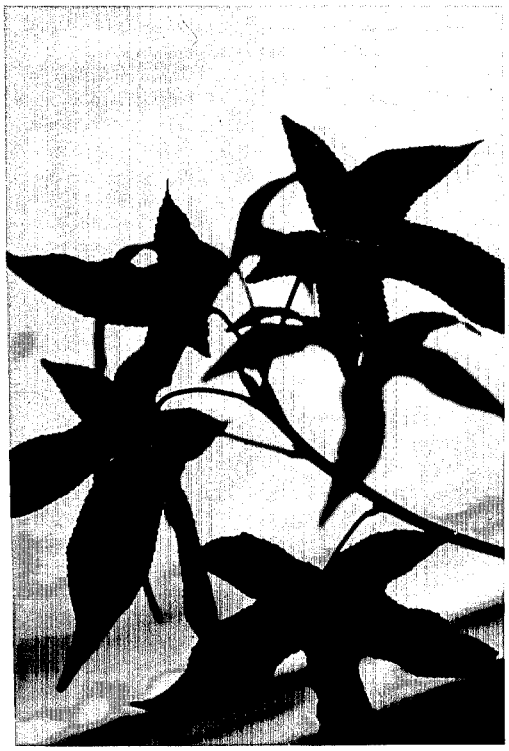
FIG. 1 is a close-up view showing the leaves regreening.

The leaves, as shown in FIG. 1, of the new variety are large and are similar to *L. styraciflua.* The leaves are from 16 to 20 cm (6 to 8 inches) in length, with petiole length an additional 8 cm (3 inches), and are 20–25 cm (8 to 10 inches) in width. The leaves are basically 5-lobed with younger more vigorously growing stock having larger and deeper lobes to the leaves.

During summer the leaves are a deep rich green (#70 ivy green to #77 forest green (blackish shade)) in color.

Figure 3:
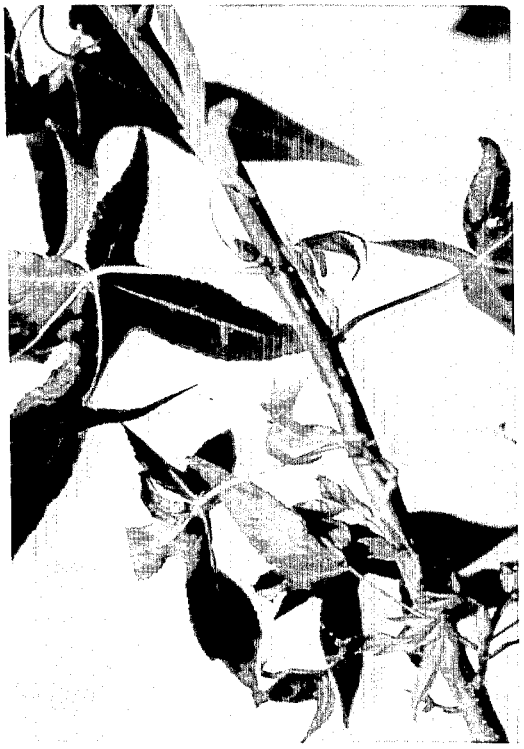
FIG. 3 shows new shoots emerging at the stem axials of leaves as viewed from the underside of the leaves.
Figure 2:
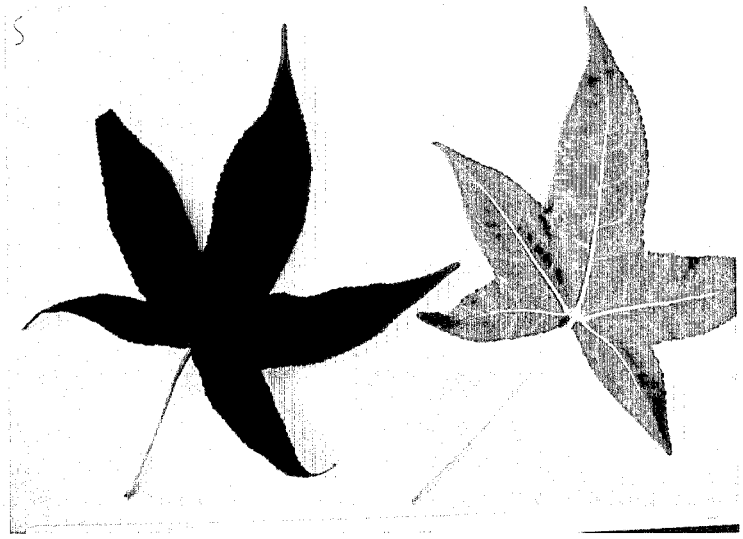
FIG. 2 is a close-up view of the upper and lower surfaces of the leaves.
Figure 4:
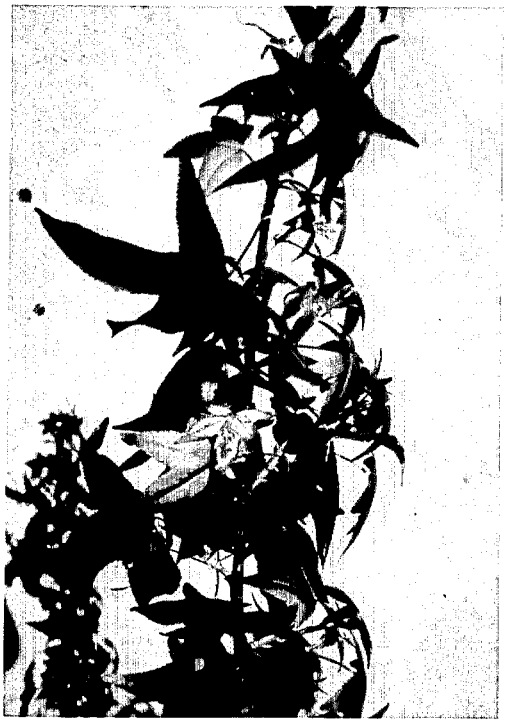
FIG. 4 shows new shoots as viewed from the upper side of the leaves.

During the winter the color of the upper surface of the leaves for about 95% of the foliage is between #42 maroon and #56 grape violet (blackish shade), while the lower surface of the leaves remains the deep rich green of summer, FIG. 2. However, where the lower surface is exposed to clear winter sunlight it takes on the rich color of the upper surface. This is shown in FIG. 3. The upper surface of the leaves return to their deep rich green color during spring. FIGS. 3 and 4 show a close-up view of the new spring shoots breaking at the stem axils. The leaves shown in FIG. 4 remain in their full fall and winter color.

Some leaves turn #10 chrome yellow to #12 burnt orange to #28 cardinal red throughout the year, and drop off while the rest of the tree is a full deep green (#70 ivy green) color. A few leaves (approximately 2% of the foliage) turn to #27 dark blood red to #34 dark wine red before they are shed.

Flowers and fruit are the same as other liquidambars, although the tree does not seem to fruit heavily at all. The mother tree, 16 years old, bears very little fruit.

Figure 5:
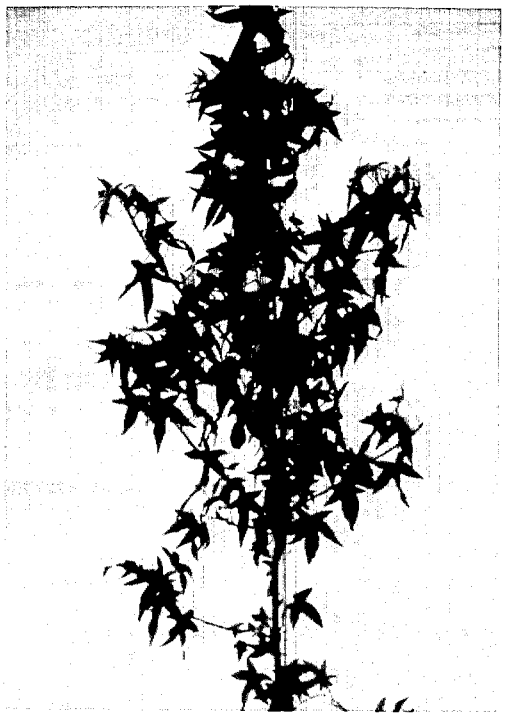
FIG. 5 is a side view of a two year old liquidambar tree of the new variety.

The height of the new variety is comparable to standard liquidambars in attaining approximately 50–80 feet in height. A two year old liquidambar of the new variety, shown in FIG. 5, is about six feet tall.

Trunk is #71 grey green, relatively smooth with a few irregularly spaced tubercles approximately 1 mm in diameter. This plant does not have the heavy corkiness seen on other Liquidambars.

I claim:

1. The new and distinct variety of liquidambar tree described, illustrated and identified by the characteristics enumerated above.

* * * * *